United States Patent [19]

Doyle

[11] 4,320,230
[45] Mar. 16, 1982

[54] METHANOL HOMOLOGATION USING IRON-COBALT CARBONYL CLUSTER CATALYST

[75] Inventor: Gerald Doyle, Whitehouse Station, N.J.

[73] Assignee: Exxon Research & Engineering Co., Florham Park, N.J.

[21] Appl. No.: 180,863

[22] Filed: Aug. 25, 1980

Related U.S. Application Data

[63] Continuation-in-part of Ser. No. 78,563, Sep. 24, 1979, abandoned.

[51] Int. Cl.³ ............... C07C 27/00; C07C 29/32; C07C 47/06
[52] U.S. Cl. .................. 568/487; 560/265; 568/902
[58] Field of Search .............. 568/902, 487

[56] References Cited

U.S. PATENT DOCUMENTS 3,332,749 7/1967 Natta et al. ............ 260/439 R
4,126,752 11/1978 Novotny et al. ........... 568/902

FOREIGN PATENT DOCUMENTS 52-73804 6/1977 Japan .
437745 1/1975 U.S.S.R. .

OTHER PUBLICATIONS

Wender, "Catal. Rev.-Sci. Eng.", 14 (1976), pp. 97–129.
Wender et al., "Science", vol. 113 (1951), pp. 206–207.
Berty et al., "Chem. Tech." (Berlin), 8 (1956), pp. 260–266.

Primary Examiner—Joseph E. Evans
Attorney, Agent, or Firm—James H. Takemoto

[57] ABSTRACT

A homogeneous catalytic process for the selective conversion of methanol to ethanol or acetaldehyde. The process comprises contacting CO and $H_2$ with a catalytically effective amount of an iron-cobalt carbonyl complex of the formula $M[FeCo_3(CO)_{12}]$ where M is hydrogen or a cation and an iodide promoter; heating the resulting mixture at temperatures of from 100° to 250° C. at pressures of from 5 to 100 MPa. By controlling the reaction parameters of $H_2$:CO ratio, temperature and reaction time, acetaldehyde or ethanol can be selectively produced.

17 Claims, 2 Drawing Figures

METHANOL HOMOLOGATION USING IRON-COBALT CARBONYL CLUSTER CATALYST

CROSS REFERENCE TO RELATED APPLICATION

This application is a continuation-in-part of copending application Ser. No. 78,563 filed Sept. 24, 1979, and now abandoned.

BACKGROUND OF THE INVENTION

1. Field of the Invention

This invention relates to a homogeneous process for the homologation of methanol to at least one of acetaldehyde, ethanol or methyl acetate. More particularly, methanol is treated with CO or $CO/H_2$ mixtures in the presence of catalytic amounts of an iron-cobalt cluster compound and an iodide promoter.

2. Description of the Prior Art

The homologation of methanol to ethanol was first described by Wender et al, *Science* 113, 206 (1951). The catalyst for the reaction was dicobalt octacarbonyl. The product selectivities and catalyst efficiencies, however, were relatively low. It was subsequently discovered that product yields could be improved by the addition of small amounts of iodide promoters (J. Berty et al, *Chem. Tech.* (Berlin), 8, 260 (1956)). The production of ethanol from methanol using ruthenium and/or osmium complexes in the presence of iodides as co-catalysts is described in Japanese Pat. No. 52-73804. The reaction of methanol with synthesis gas has been discussed by I. Wender in *Catal. Rev-Sci. Eng.*, 14, 97 (1976).

The carbonylation of methanol to acetic acid and methyl acetate using a cobalt acetate-iron acetate catalyst is described in Russian Pat. No. 437745. U.S. Pat. No. 3,332,749 (G. Natta and P. Chini) discloses iron-cobalt metallocarbonyl compounds of the formula $R[FeCo_3(CO)_{12}]$ where R is a cation or H.

It would be desirable to convert methanol to ethanol, acetaldehyde or methyl acetate with a high degree of selectivity thus avoiding the substantial amounts of broad product mixture characteristic of known catalysts, especially heterogeneous catalysts. Moreover, the catalyst should function with a relatively high degree of catalyst efficiency with respect to methanol conversion.

SUMMARY OF THE INVENTION

In one aspect of the invention, it has been discovered that the selective catalytic homologation of methanol can be accomplished by contacting CO and $H_2$ with an iron-cobalt cluster compound. Accordingly, the present process for the homogeneous catalytic conversion of methanol to ethanol, acetaldehyde or mixtures thereof comprises contacting methanol with CO and $H_2$ at a $CO:H_2$ mole ratio of from 1:10 to 10:1, in the presence of a catalytically effective amount of an iron-cobalt carbonyl cluster complex and an effective amount of an iodide promoter, and heating the resulting mixture to a temperature of from about 100° to 250° C. at a pressure of from about 5 to 100 MPa.

Another aspect of the invention relates to a process for the homogeneous catalytic conversion of methanol to methyl acetate, which comprises contacting methanol with carbon monoxide in the presence of a catalytically effective amount of an iron-cobalt carbonyl cluster complex and an effective amount of an iodide promoter, and heating the resulting mixture to a temperature of from about 100° to 250° C. at a pressure of from about 5 to 100 MPa.

Homogeneous catalytic reactions employing an iron-cobalt cluster compound and CO or $CO/H_2$ mixtures provide a selective method of producing acetaldehyde, ethanol and methyl acetate together with small amounts of by-products such as dimethyl and methyl ethyl ether, ethyl acetate, butanal, butenal, methane and other low molecular weight oxygenates. In the present process, using $CO/H_2$ mixtures as reactants, lower temperatures, lower $H_2:CO$ ratios and shorter reaction times generally favor the formation of acetaldehyde while ethanol formation is favored by higher temperatures, higher $H_2:CO$ ratios and longer reaction times. In the case of methyl acetate synthesis, only CO and methanol are present as reactants. Since none of the products requiring $H_2$ are formed, the formation of the desired product is substantially the only reaction which occurs under the instant reaction conditions.

While a number of hydrocarbons and oxygenated derivatives thereof can be manufactured from synthesis gas, i.e., CO and $H_2$, and heterogeneous catalysts using the Fischer-Tropsch reaction, the selectivity is usually low and a broad spectrum of compounds is obtained. The present catalyst system employs inexpensive materials whereas other homogeneous homologation catalysts use relatively expensive metals such as rhodium and ruthenium.

DETAILED DESCRIPTION OF THE INVENTION

Figure 1:
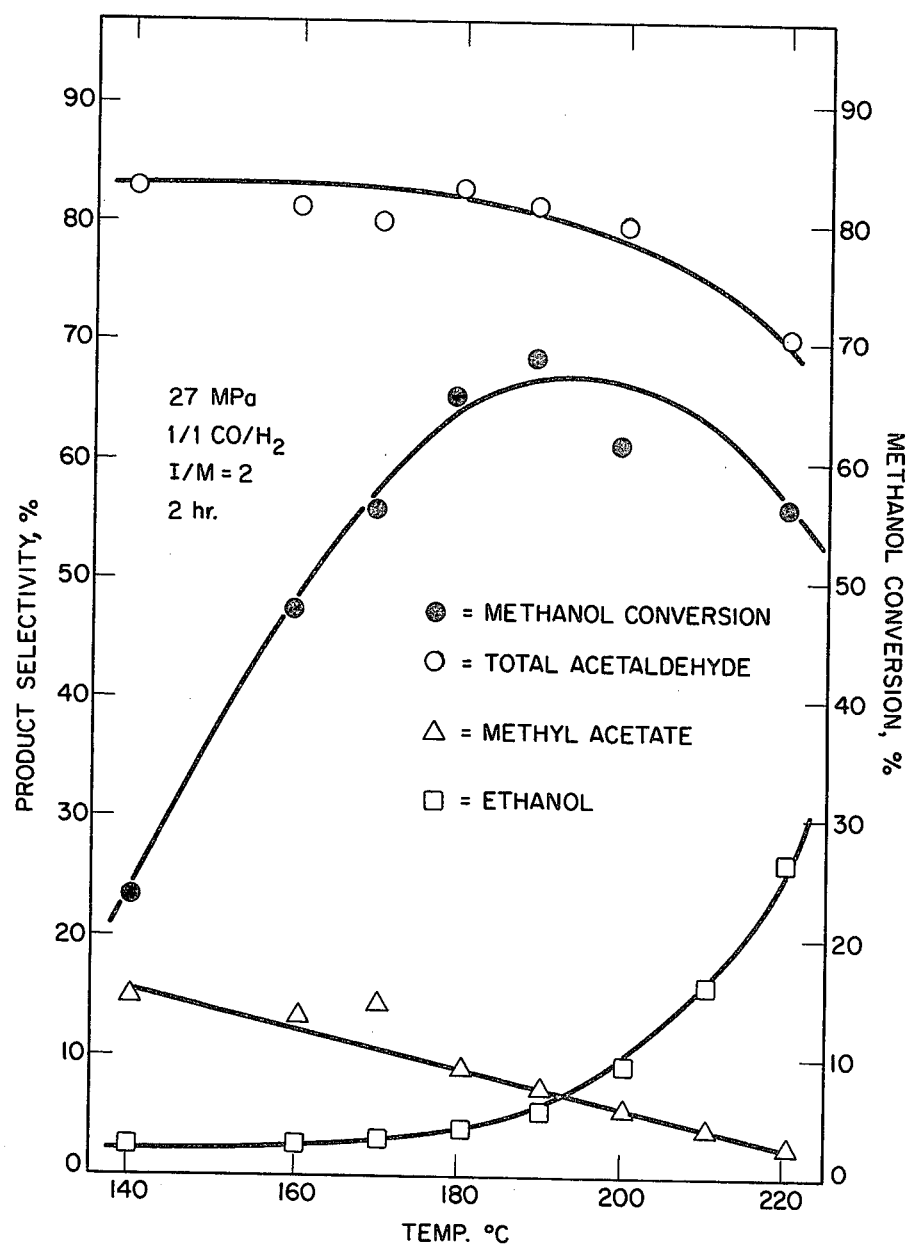
FIG. 1 is a graph of the effect of temperature on methanol conversion and product selectivity.

The present process for the homogeneous catalytic conversion of methanol employs iron-cobalt carbonyl cluster compounds. Preferred Fe—Co carbonyl cluster compounds have the formula

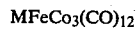

$MFeCo_3(CO)_{12}$ wherein M is hydrogen or a cation. Examples of suitable cations include alkali metal, $(C_6H_5)_3PNP(C_6H_5)_3^\oplus$, salts of $C_3$ to $C_9$ heterocyclic rings containing nitrogen, e.g., pyrrole, pyridine, pyrazole, oxazole, pyrazine, indole and quinoline, $R_1R_2R_3R_4N^\oplus$, $R_1R_2R_3R_4P^\oplus$ or $R_1R_2R_3R_4As^\oplus$ where $R_1$ to $R_4$ are each hydrogen, $C_1$ to $C_{20}$ alkyl, $C_3$ to $C_8$ cycloalkyl, benzyl, phenyl or phenyl substituted by lower ($C_1$-$C_6$) alkyl, lower alkoxy or halogen. Other known Fe—Co carbonyl cluster compounds have the formula $MCoFe_3(CO)_{13}$ where M has the definition set forth above. It is preferred that the cation be other than hydrogen.

Examples of Fe—Co carbonyl cluster compounds are $HFeCo_3(CO)_{12}$, $Na[FeCo_3(CO)_{12}]$, $K[FeCo_3(CO)_{12}]$, $(C_4H_9)_4N[FeCo_3(CO)_{12}]$, $(C_2H_5)_4N[FeCo_3(CO)_{12}]$, $(C_4H_9)_4P[FeCo_3(CO)_{12}]$, $(\phi)_4P[FeCo_3(CO)_{12}]$, $(\phi)_3PCH_3[FeCo_3(CO)_{12}]$, $\phi_3PNP\phi_3[FeCo_3(CO)_{12}]$, $(C_2H_5)_3NCH_2C_6H_5[FeCo_3(CO)_{12}]$, $(C_2H_5)_3NH[FeCo_3(CO)_{12}]$,

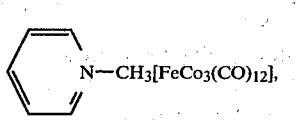

$HCoFe_3(CO)_{13}$, $(C_4H_9)_4N[CoFe_3(CO)_{13}]$ and $\phi_3PNP\phi_3[CoFe_3(CO)_{13}]$. Species wherein M is not hydrogen are preferred.

The Fe—Co carbonyl cluster compounds are employed in a catalytically effective amount which encompasses a broad concentration range of from about 0.0001 to 0.1 M, preferably 0.001 to 0.01 M. Higher concentrations are technically feasible but do not result in any particular advantage.

The cluster compounds are prepared by known methods. For example, $Co_2(CO)_8$ can be reacted with $Fe(CO)_5$ in acetone and the resulting acetone complex converted to the acidic form by treatment with strong acid or to salts by ion exchange reactions.

While not wishing to be bound by any theoretical or mechanistic discussion, it appears possible that Fe—Co carbonyl cluster compound functions as a catalyst precursor. This is suggested by the fact that almost no original cluster compound can be detected from an analysis of the reaction mixture obtained after completion of the reaction. Such an analysis, however, is made at room temperature and pressure and therefore provides no accurate indication of what species exists under actual reaction conditions.

The active catalytic complex may be the Fe—Co carbonyl cluster compound itself, a derivative thereof formed under reaction conditions or separate Fe and Co carbonyl complexes formed by the decomposition of the cluster compound. In any event, the active catalytic complex(es), if not the parent carbonyl cluster compound, exists only under reaction conditions, i.e., elevated temperatures and pressures. The use of $Fe(CO)_5$, $Co_2(CO)_8$ or mixtures thereof as catalysts does not result in the superior selectivities and catalyst efficiencies possible from using Fe—Co carbonyl cluster compounds unless there is a stabilizing cation present. It is probable that $Fe(CO)_5$ and $Co_2(CO)_8$ enter into an equilibrium reaction at room temperature to form a Fe—Co complex. That equilibrium, however, is shifted in favor of the reactants at elevated temperatures and $CO/H_2$ pressure. This would account for the fact that mixtures of $Fe(CO)_5$ and $Co_2(CO)_8$ are not good methanol homologation catalysts even in the presence of a $CH_3I$ promoter. On the other hand, it has been discovered that the equilibrium forming a Fe—Co complex can be stabilized in favor of the complex in the presence of a cation, e.g., $(C_4H_9)_4N^{\oplus}$. The latter system containing stabilizing cation is an efficient catalyst for methanol homologation and can form the basis for an in situ generation of catalyst. It is therefore evident that the present catalytic action is not simply the result of the decomposition of the Fe—Co carbonyl cluster compound into the iron and cobalt carbonyl complexes used to prepare the cluster compound.

The present homologation reaction is promoted by iodides. Suitable iodide promoters include HI, alkyl iodides such as $CH_3I$, $CH_3CH_2I$, $(CH_3(CH_2)_2I$ and $CH_3(CH_2)_3I$, alkali metal iodides, tetraalkylammonium iodides, tetraalkyl or tetraphenyl phosphonium iodides, tetraalkyl or tetraphenyl arsonium iodides, or mixtures thereof. Hydrogen iodide and methyl iodide are preferred promoters. The alkyl in the tetraalkylammonium, tetraalkyl phosphonium and tetraalkyl arsonium salts denotes to $C_1$ to $C_{20}$ and alkyl iodides are $C_1$–$C_{10}$, preferably $C_1$–$C_6$ in the alkyl.

The preferred temperature range is from 140° to 220° C. At temperatures above 250° C., substantial decreases in methanol conversions are observed which can probably be attributed to decomposition of the catalyst. Generally, acetaldehyde formation is favored by a lower temperature range of from about 140° to 200° C. whereas the preferred temperature range for ethanol is higher, i.e., 200° to 220° C.

The pressure can vary over wide ranges with pressures of from about 20 to 50 MPa being preferred. Below about 5 MPa, the rate of reaction is very slow whereas very high pressures such as those in excess of about 100 MPa require special expensive equipment. With respect to the formation of acetaldehyde and ethanol, higher pressures favor an increased conversion of methanol. There is also an increase in selectivity to acetaldehyde with increasing pressure whereas ethanol selectivity is almost unaffected. Accordingly, it would be most preferred to operate at as high a pressure as is economically feasible.

The ratio of iodide to metal (I:M) can affect the methanol conversion and product selectivity. The I:M ratio is the number of moles of iodide per total number of gram atoms of metal present (Fe+Co). The I:M ratio is therefore four times the ratio of the number of moles of iodide per number of moles of catalyst. Below an I:M ratio of 0.5:1, there is a sharp decrease in both methanol conversion and product selectivity. High ratios can lead to decreases in acetaldehyde selectivity and the formation of condensation products whereas ethanol selectivity is virtually unaffected. The I:M ratio can vary from 0.5:1 to 100:1, preferably from 2:1 to 10:1.

The reaction period varies from about 0.1 to 24 hours. If acetaldehyde is the desired product, shorter reactions of from 0.5 to 3 hours are preferred. For ethanol, the preferred reaction times are from 3 to 10 hours. The reaction time is, of course, dependent on other reaction parameters, e.g., temperature and $H_2:CO$ ratio.

The initial reaction mixture is charged with CO and $H_2$ at an $H_2:CO$ mole ratio of from 1:10 to 10:1, preferably 1:5 to 5:1. If methyl acetate is the desired product, $H_2$ is omitted from the reaction mixture. The stoichiometry of the reaction for conversion of methanol to acetaldehyde suggests an approximate 1:1 $H_2:CO$ ratio. Increasing the amount of $H_2$ relative to CO, e.g., 3:2, favors the formation of ethanol.

The reaction is preferably run with methanol as solvent. The amount of methanol is not critical provided there is sufficient methanol present to serve as reactant in the homologation reaction. Other organic solvents which are inert under the reaction conditions may be employed, e.g., aromatics such as benzene, toluene and xylene and ethers such as diethyl ether, tetrahydrofuran, 1,2-dimethoxyethane. There is generally no advantage to adding a solvent other than methanol.

The process may be conducted in a batchwise or continuous manner in a conventional high pressure reactor equipped with heating means. In general, the reactor is charged with methanol containing dissolved Fe—Co carbonyl cluster compound, flushed with reactant gas, i.e., CO and/or $H_2$ and then pressurized. The reactor is agitated to ensure good mixing and heated to the desired temperature. Pressure adjustments are then made, if necessary. After the desired reaction times, the reactor is cooled and the contents isolated and worked up using conventional isolations techniques such as distillation. If methyl acetate is the desired product, the reactor is charged with CO only.

While not wishing to limit the invention to any particular reaction mechanism, the above conditions with respect to reaction parameters may be explained as follows. The first product formed in the homologation of methanol is probably acetaldehyde, which is formed from the reduction of a catalytic intermediate into which CO has been inserted. Acetaldehyde can react with methanol to form an acetal but the acetal will react with water to regenerate acetaldehyde. Acetaldehyde is a reactive species and can be further reduced to ethanol. On the other hand, it is known that ethanol is much less reactive to homologation than is methanol.

Since the reduction of acetaldehyde is the more difficult reaction, it can be seen that if high selectivity to acetaldehyde is desired, one should use lower temperatures, shorter reaction times and $CO:H_2$ ratios wherein excess $H_2$ is avoided. In contrast, if ethanol is the desired product, higher temperatures, longer reaction times and higher $H_2:CO$ ratios to provide excess hydrogen are desirable so that acetaldehyde is reduced. Preferred conditions for acetaldehyde formation are temperatures of from 140° to 200° C., an $H_2:CO$ ratio from about 0.5:1 to 1:1 reaction times of from 1 to 3 hours, whereas preferred ethanol reaction conditions are temperatures of from 200° to 220° C., $H_2:CO$ ratios of from 3:1 to 1.5:1 and reaction times of from 3 to 10 hours.

If methyl acetate is desired, then $H_2$ is eliminated. In this manner, methanol reacts directly with the catalytic intermediate into which CO has been inserted to form the ester rather than forming acetaldehyde. Since no products requiring $H_2$ can theoretically be formed, it is expected that the reaction to form methyl acetate would produce minimal by-products and this is the observed result. In fact, it is possible to follow the rate of disappearance of methanol with time and to calculate a pseudo first-order rate constant for the reaction.

The process of the invention is further illustrated in the following examples.

EXAMPLES

General Procedure $HFeCo_3(CO)_{12}$ and its salts were prepared by methods described in the literature (P. Chini et al, U.S. Pat. No. 3,332,749; *Gazz Chim. Ital.*, 90, 1005 (1960)). Reagent grade methanol and toluene were used without purification. The high pressure reactions were carried out in a 1-liter stirred autoclave equipped with a catalyst blowcase and directly fed by high pressure syn-gas lines. The autoclave was charged with methanol containing toluene as an internal standard for chromatography and an appropriate amount of methyl iodide as promoter, and was preheated to reaction temperature. The catalyst, dissolved in methanol, was then introduced through the blowcase, and the pressure immediately brought to the desired level. Liquid samples were taken at desired intervals during the reaction and a gas sample taken at the conclusion of the reaction.

Gas and liquid products were analyzed by gas chromatography using a Perkin-Elmer Model 900 or a Hewlett-Packard model 5840A instrument. Columns packed with Chomosorb 102 or Carbowax 20M on Gas Chrom Q were used with temperature programming. Peaks were identified by comparing to known compounds on two different columns if possible. For peaks which could not be identified in this manner, identification was made by gas-chromatography-mass spectroscopy.

Quantitative measurements were made using toluene as an internal standard. Response factors were either determined experimentally or were taken from known compilations (Dietz, *J. Gas. Chrom.*, 5:68 (1967)).

EXAMPLE 1

This example was conducted to demonstrate the conversion of methanol to acetaldehyde. An autoclave was charged with methanol containing $CH_3I$ in a $CH_3I:(Fe+Co)$ ratio of 4:1 heated to 180° C. and charged with methanol containing 2 mmoles of $(C_4H_9)_4N[FeCo_3(CO)_{12}]$. The total amount of methanol was 8.66 moles. The autoclave was pressurized to 27 MPa using a 1:1 $CO:H_2$ mixture. The reaction was allowed to proceed for 0.5 hour and then terminated by cooling. The products were analyzed by gas chromatography and the results are summarized as follows.

TABLE I

SAMPLE CALCULATIONS FOR METHANOL CONVERSION[A], PRODUCT SELECTIVITY[B], AND MASS BALANCE[C]

| Compound | Products Moles | Wt. (g) | Product Selectivity % | Methanol Consumed in Product Moles | Wt. (g) | Gas Consumed in Product CO Moles | Wt. (g) | $H_2$ Moles | Wt. (g) |
|---|---|---|---|---|---|---|---|---|---|
| Methanol | 4.84 | 154.9 | | 4.84 | 154.9 | | | | |
| Acetaldehyde | 1.55 | 68.2 | 62 | 1.55 | 49.7 | 1.55 | 38.8 | 1.55 | 3.1 |
| Ethanol | 0.10 | 4.6 | 4 | .10 | 3.2 | .10 | 2.8 | .20 | .4 |
| Methyl Acetate | 0.32 | 23.7 | 13 | .64 | 20.5 | .32 | 9.0 | | |
| Dimethyl Acetal | 0.44 | 39.6 | 18 | 1.32 | 42.3 | .44 | 12.3 | .44 | .9 |
| Water | 3.07 | 55.6 | | | | | | | |
| Others (as butanol) | 0.10 | 7.4 | | .20 | 6.4 | .20 | 5.6 | .40 | .8 |
| | | 353.7 | | 8.65 | 277.0 | | 68.5 | | 5.2 |

[A]Methanol Conversion = (8.66 − 4.84)/8.66 = 44%

[B]Product Selectivity = Moles Individual Product/Total Moles of New Products Containing Methanol = $\frac{\text{Moles of Ind. Prod.}}{2.51}$

[C]Mass Balance = $\left[1 - \frac{\text{Wt. of Products} - \text{Wt. of Reactants}}{\text{Wt. of Products}}\right] = \left[1 - \frac{353.7 - 350.8}{353.7}\right] \times 100 = 99.2\%$ As the data demonstrate, the main product is acetaldehyde with methyl acetate and dimethyl acetal as the predominant by-products. The reaction time, however, is short (0.5 hr) and if the reaction were allowed to proceed for a longer period, dimethyl acetal would be directly converted to acetaldehyde, by reaction with water. This would greatly increase the selectivity to acetaldehyde.

EXAMPLE 2

This example illustrates the effect of temperature on methanol conversion and product selectivity. The general procedure set forth in Example 1 was followed except that the I:M ratio is 2, the reaction time is 2 hours and the reaction run at different temperatures.

The results are shown in FIG. 1. Under the particular reaction conditions involved, the figure indicates that the reaction rate and hence the methanol conversion per unit time steadily increases with temperature. At temperatures above 200° C., however, the overall methanol conversion begins to decrease. The reason for this decrease is not certain but is probably due to thermal decomposition of the catalyst at elevated temperatures. Above 250° C., the decrease is pronounced.

The graph further indicates that above a temperature of about 180° C., selectivity to acetaldehyde decreases whereas that to ethanol increases. It should be kept in mind that the $CO:H_2$ ratio is 1:1 and the reaction time is 2 hours, both parameters being more favorable to acetaldehyde formation as compared to ethanol.

In order to maximize acetaldehyde yields, one would choose a temperature of approximately 180° under these conditions. At this temperature, the methanol conversion is nearly at a maximum and acetaldehyde selectivity has not yet begun to fall off significantly.

EXAMPLE 3

This example studies the effect of pressure on methanol conversion and product selectivity. The procedure of Example 2 was followed except that the temperature was 140° to 160° C., and pressure varied over the range from 1000 to 4000 psi. At these temperatures, there is nearly linear dependence of pressure on methanol conversion, i.e., the higher the pressure, the higher the methanol conversion. The product selectivities at 140° C. show a gradual trend to higher acetaldehyde yields at higher pressures, but the influence is not marked as the selectivities range from 70 to 80% over the entire pressure range studied. Methyl acetate is the only significant by-product formed. Ethanol product selectivity is only very slightly dependent on pressure, the increase in selectivity being less than about 2%.

EXAMPLE 4

The effect of varying the ratio of methyl iodide added on both methanol conversion and product selectivity is described in this example. The I:M ratio is equal to the number of moles of iodide added per total number of gram atoms of metal present Fe+Co). The conditions are those of Example 2 at a temperature of 180° C.

There is a nearly linear increase in the methanol conversions from about 50% to 70% as one increases the amount of methyl iodide (similar results are also seen for hydrogen iodide) added from an I:M ratio of 2:1 to 16:1. Below an I:M ratio of two, a sharp decrease in conversion is observed.

The acetaldehyde selectivity shows a maximum at a I:M ratio of approximately 6. At higher ratios, the acetaldehyde selectivity exhibits a gradual decline due mainly to the formation of higher molecular weight condensation products. Low I:M ratios result in somewhat larger amounts of ethanol but methyl acetate is little effected by changes in the I:M ratio at these conditions.

In order to maintain high acetaldehyde selectivity with reasonably high methanol conversions, an I:M ratio of between 4 and 8 seems optimum, for the set of conditions chosen. Ethanol selectivity shows little dependence on I:M ratio.

EXAMPLE 5

This example is directed to the effects of gas composition on product selectivity. The experimental procedure was that of Example 2. At a temperature of 180° C., increasing the syn-gas feed from a 50:50 $H_2$ to CO ratio to 60:40 results in a lower rate of methanol conversion by about 10 to 20%. At the same time, an increase in the proportion of ethanol vs. acetaldehyde is noted at any given reaction time. These results are consistent with the theory that acetaldehyde is the first formed product and is subsequently reduced to ethanol. By increasing the amount of hydrogen relative to carbon monoxide, one favors the latter reaction.

It is noted that 180° C. is a temperature that favors acetaldehyde formation (see Example 2). At a temperature of 220° C., both the rate of methanol conversion and ethanol selectivity are considerably higher and with a 60:40 $H_2$:CO ratio and reaction times of about 4–6 hours, ethanol selectivities of 60–80% are possible.

EXAMPLE 6

The reaction time influences both the methanol conversion and product selectivity. The general procedure of Example 2 was followed with the following parameters: Temp.=220° C.; Pressure=27 MPa; I:M=2; Cluster Compound=$(C_4H_9)_4N[FeCo_3(CO)_{12}]$, 1 mmole in 150 ml methanol; $H_2$:CO=50:50.

Figure 2:
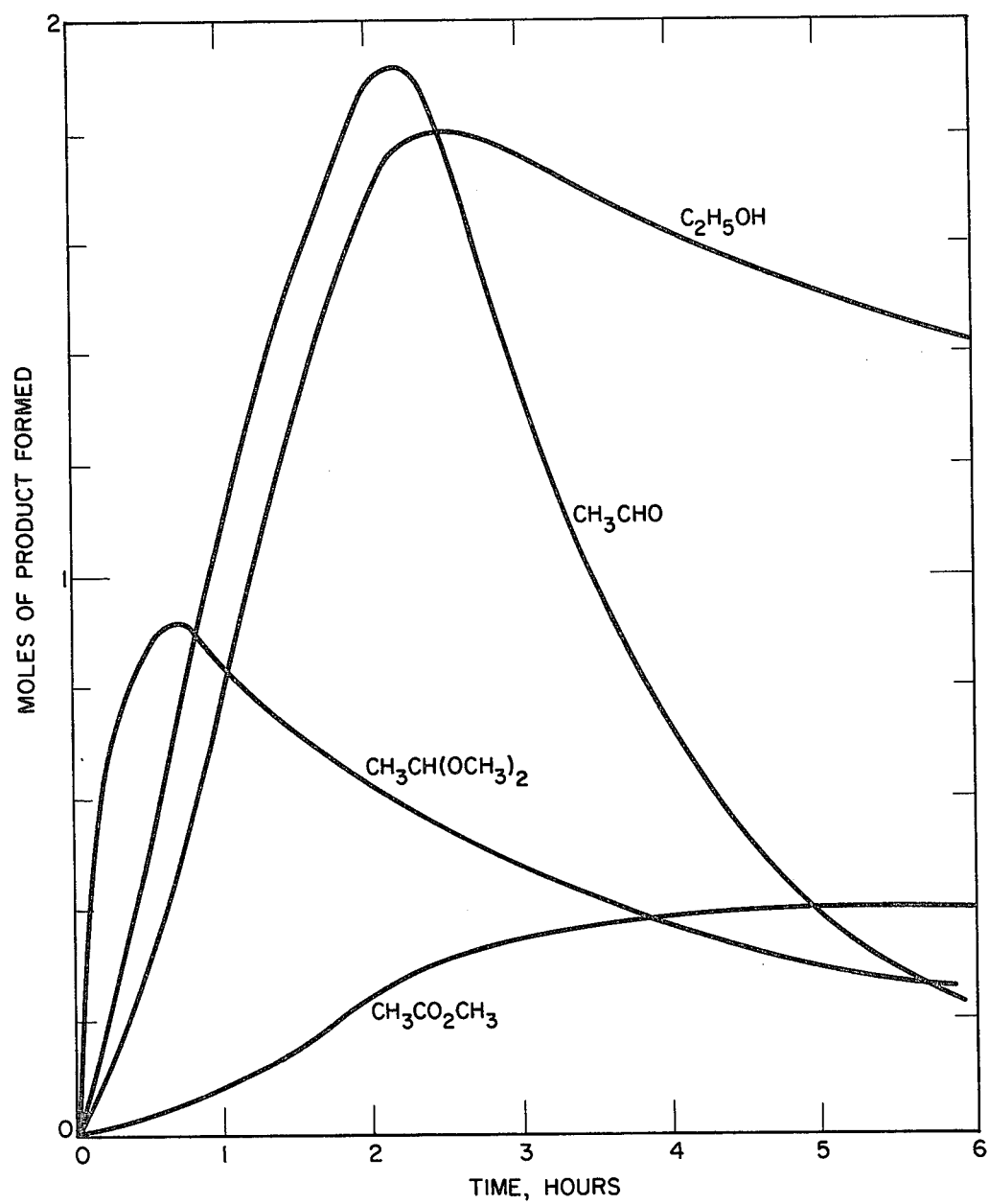
FIG. 2 is a graph of product formation as a function of reaction time.

FIG. 2 is a graph of the products obtained as a function of time. At a temperature of 220° C., it can be seen that acetaldehyde production reaches a maximum and then rapidly decreases. In the reaction period between 2.5 and 6 hours, the product ratio of ethanol:acetaldehyde ratio steadily increases. Thus, longer reaction times favor ethanol formation, particularly at higher temperatures.

EXAMPLE 7

This example was conducted to demonstrate the production of ethanol under favorable conditions. The procedure of Example 6 was followed, except that the $H_2$:CO ratio was increased to 60:40. The reaction time was 6 hours. The results are summarized in Table II.

TABLE II

| Product | Approximate Percentage of Methanol Converted |
|---|---|
| Dimethyl ether | 2 |
| Methyl ethyl ether | 3 |
| Acetaldehyde | 6 |
| Ethanol | 70 |
| Methyl acetate | 4 |
| Ethyl acetate | 2 |
| Butanal | 2 |
| Butenal | 5 |
| Methane | 3 |
| Other | 4 |

Table II is a summary of the product distribution in terms of the percentage of methanol converted. Ethanol is by far the dominant product with acetaldehyde being formed in amounts less than 10% the amount of ethanol.

Small amounts of by-products are also formed under the conditions favoring ethanol formation. These results represent a methanol conversion of 75% and a selectivity to ethanol of 73% vs. 10% for acetaldehyde.

EXAMPLE 8

This example is directed to a showing that the active catalyst species is not a mixture of $Fe(CO)_5$ plus $Co_2(CO)_8$. Example 7 was repeated except that the carbonyl compounds employed as catalyst were varied. The results are summarized in Table III.

TABLE III

METHANOL HOMOLOGATION WITH Fe-Co COMPLEXES

| Catalyst | Methanol Conversion | Selectivity To Ethanol | Acetaldehyde |
|---|---|---|---|
| $Co_2(CO)_8$ | 9 | 30 | 40 |
| $Fe(CO)_5$ | 2 | 30 | 60 |
| $Co_2(CO)_8 + Fe(CO)_5$ | 11 | 50 | 40 |
| $(C_4H_9)_4N[FeCo_3(CO)_{12}]$ | 75 | 73 | 10 |
| $H[FeCo_3(CO)_{12}]$ | 16 | 47 | 43 |

The results of Table III clearly indicate that the salt $(C_4H_9)_4N[FeCo_3(CO)_{12}]$ is not the equivalent of a mixture of $Co_2(CO)_8+Fe(CO)_5$ in terms of methanol conversion or ethanol selectivity. The cluster salts are generally better homologation catalysts (or catalyst precursors) than the parent acid, i.e., $HFeCo_3(CO)_{12}$. This may be a reflection of the greater stability of the salt over the acid.

EXAMPLE 9

The synthesis of methyl acetate can be achieved in high yields and purity as described below. A 1-liter stirred autoclave was charged with a solution containing 250 ml methanol, 50 ml toluene and 2.27 g $CH_3I$. The autoclave was then pressurized to 10 MPa with carbon monoxide and heated to 180° C. A solution containing 0.81 g (n—$C_4H_9)_4N[Fe(CO)_{12}Co_3]$ dissolved in 100 ml methanol was then pressurized into the reactor and the pressure was adjusted to 27 MPa. The reaction was allowed to proceed at 180° C. with additional CO being added automatically in order to keep the pressure constant at 27 MPa. Liquid samples were taken at regular intervals for analysis by gas chromatography. After three hours, analysis indicated that 29% of the methanol had reacted with 96% selectivity to methyl acetate.

After eight hours, the methanol conversion was 63% with a selectivity of 96% to methyl acetate.

None of the products requiring $H_2$ are formed and methyl acetate is essentially the only product formed. At high temperatures and long reactions, small amounts of ethanol and acetaldehyde can be detected. This may be due to a reaction between water and CO to form $H_2$ which results in the homologation reaction.

EXAMPLE 10

The preparation of acetaldehyde using an in situ generated iron-cobalt carbonyl complex is illustrated as follows. A solution containing 0.20 g $Fe(CO)_5$, 0.51 g $Co_2(CO)_8$ and 0.37 g $(C_4H_9)_4NI$ in 100 ml methanol was prepared. This catalyst solution was added under $CO/H_2$ pressure to a stirred autoclave containing 250 ml methanol, 50 ml toluene and 2.13 g $CH_3I$ previously heated to 180° C. under 28 MPa pressure of 1:1 $CO/H_2$. The reaction was allowed to proceed for 2 hours at which time the products were sampled and analyzed. The analysis showed a 52% conversion of methanol and a liquid product selectivity of 77% to acetylaldehyde, 11% to methylacetate, 10% to dimethyl acetal and 2% to ethanol.

A similar experiment was carried out in which a solution of 0.81 g $(C_4H_9)_4NFeCo_3(CO)_{12}$ in 100 ml methanol was added to a stirred autoclave containing 250 ml methanol, 50 ml toluene and 2.27 g $CH_3I$ under conditions identical to those described above. (The amounts of reagents used were chosen such that the weights of Fe, Co, N and I and the Fe:Co:N:I: ratio would be nearly identical in both experiments). The liquid products were sampled and analyzed after two hours reaction time. The results show a methanol conversion of 52% and a liquid product selectivity of 77% to acetylaldehyde, 12% to methyl acetate, 4% to dimethylacetyl and 6% to ethanol.

These experiments demonstrate that mixtures of $Fe(CO)_5$, $Co_2(CO)_8$, which can react in situ to form the $FeCo_3(CO)_{12}^-$ anion, are effective catalysts for the conversion of methanol with $CO/H_2$ if a stabilizing cation is present. The activity and selectivity of these mixtures are similar to those observed with preformed $FeCo_3(CO)_{12}^-$ salts.

EXAMPLE 11

This example compares the activity and selectivity of a number of different salts of the $[FeCo_3(CO)_{12}]^-$ anion. The reaction was carried out in the same manner as described in Example 1, except that in each case the product was sampled after one hour. The results are summarized in the following table which demonstrates that salts of $[FeCo_3(CO)_{12}]^-$ with cations other than $(C_4H_9)_4N^{\oplus}$ are effective catalysts.

TABLE IV

| Catalyst | Methanol Conversion per cent | Product Selectivity Percent Total Acetaldehyde* | Methyl Acetate |
|---|---|---|---|
| $(C_6H_5)_3PNP(C_6H_5)_3[FeCo_3(CO)_{12}]$ | 38 | 83 | 14 |
| $(C_2H_5)_4N[FeCo_3(CO)_{12}]$ | 40 | 86 | 12 |
| $(C_6H_5)_4As[FeCo_3(CO)_{12}]$ | 42 | 84 | 14 |
| $(C_4H_9)_4N[FeCo_3(CO)_{12}]$ | 40 | 87 | 11 |
| $Cs[FeCo_3(CO)_{12}]$ | 37 | 85 | 12 |

*Acetaldehyde plus dimethylacetal

What is claimed is:
1. A process for the homogeneous catalytic conversion of methanol to ethanol, acetaldehyde or mixtures thereof which comprises:
   (a) contacting methanol with carbon monoxide and hydrogen at a hydrogen to carbon monoxide mole ratio of from 1:10 to 10:1 in the presence of a catalytically effective amount of an iron-cobalt carbonyl cluster complex and an effective amount of an iodide promoter; and

(b) heating the mixture of step (a) to a temperature of about 100° to 250° C. at a pressure of from 5 to 100 MPa.

2. The process of claim 1 wherein the iron-cobalt carbonyl cluster complex has the formula $$M[FeCo_3(CO)_{12}] \text{ or } M[CoFe_3(CO)_{13}]$$

wherein M is hydrogen, alkali metal cation, $(C_6H_5)_3PNP(C_6H_5)_3^{\oplus}$, salts of $C_3$ to $C_9$ heterocyclic ring compounds containing nitrogen, $R_1R_2R_3R_4N^{\oplus}$, $R_1R_2R_3R_4P^{\oplus}$ or $R_1R_2R_3R_4As^{\oplus}$ wherein $R_1$ to $R_4$ are each hydrogen, $C_1$ to $C_{20}$ alkyl, $C_3$ to $C_8$ cycloalkyl, benzyl, phenyl or phenyl substituted by lower alkyl, lower alkoxy or halogen.

3. The process of claim 1 wherein the iron-cobalt carbonyl complex is $(C_4H_9)_4N[FeCo_3(CO)_{12}]$.

4. The process of claim 1 wherein the concentration of iron-cobalt carbonyl complex is from 0.0001 M to 0.1 M.

5. The process of claim 1 wherein the temperature is from 140° to 220° C.

6. The process of claim 1 wherein the promoter is at least one of alkyl iodide, hydrogen iodide, tetraalkylammonium iodide, tetraalkyl phosphonium iodide, tetraphenyl phosphonium iodide, tetraalkyl arsonium iodide or tetraphenyl arsonium iodide.

7. The process of claim 1 wherein the ratio of moles of iodide to gram atoms of iron plus cobalt is from 0.5:1 to 100:1.

8. The process of claim 1 wherein the reaction is heated from 0.1 to 24 hours.

9. The process of claim 1 wherein the ethanol is the product and the mole ratio of hydrogen to carbon monoxide is from 1.5:1 to 3:1.

10. The process of claim 9 wherein the temperature is from about 200° to 220° C.

11. The process of claim 9 wherein the mixture is heated for from 3 to 6 hours.

12. The process of claim 1 wherein the product is acetaldehyde and the hydrogen to carbon monoxide ratio is from 0.5:1 to 1:1.

13. The process of claim 12 wherein the temperature is from about 140° to 200° C.

14. The process of claim 12 wherein the mixture is heated for from 1 to 3 hours.

15. The process of claim 2 wherein the iron-cobalt carbonyl complex is generated in situ from iron and cobalt compounds capable of forming the iron-cobalt carbonyl complex in the presence of an M cation.

16. A process for the homogeneous catalytic conversion of methanol to ethanol, acetaldehyde or mixtures thereof which comprises:
(a) contacting methanol with carbon monoxide and hydrogen at a hydrogen to carbon monoxide mole ratio of from 1:10 to 10:1 in the presence of a catalytically effective amount of an iron-cobalt carbonyl cluster complex of the formula $$M[FeCo_3(CO)_{12}]$$

wherein M is alkali metal cation, $(C_6H_5)_3PNP(C_6H_5)_3^{\oplus}$, salts of $C_3$ to $C_9$ heterocyclic ring compounds containing nitrogen $R_1R_2R_3R_4N^{\oplus}$, $R_1R_2R_3R_4P^{\oplus}$ or $R_1R_2R_3R_4As^{\oplus}$ where $R_1$ to $R_4$ are each hydrogen, $C_1$ to $C_{20}$ alkyl, $C_3$ to $C_8$ cycloalkyl, benzyl, phenyl or phenyl substituted by lower alkyl, lower alkoxy or halogen and an effective amount of an iodide promoter; and
(b) heating the mixture of step (a) to a temperature of about 100° to 250° C. at a pressure of from 5 to 100 MPa.

17. A process for the homogeneous catalytic conversion of methanol to ethanol, acetaldehyde or mixtures thereof which comprises:
(a) contacting methanol with carbon monoxide and hydrogen at a hydrogen to carbon monoxide mole ratio of from 1:10 to 10:1 in the presence of a catalytically effective amount of $(C_4H_9)_4N[FeCo_3(CO)_{12}]$ and an effective amount of an iodide promoter; and
(b) heating the mixture of step (a) to a temperature of about 100° to 250° C. at a pressure of from 5 to 100 MPa.

* * * * *